US012620459B2

(12) United States Patent
Wang et al.

(10) Patent No.: US 12,620,459 B2
(45) Date of Patent: May 5, 2026

(54) HIGH EFFICACY FUNCTIONAL INGREDIENT BLENDS

(71) Applicant: Stokely-Van Camp, Inc., Chicago, IL (US)

(72) Inventors: Jenna Wang, Shelton, CT (US); Tsz-Ching (James) Yuan, Yorktown Heights, NY (US); Lei Zhao, Nanuet, NY (US); Lara Nyman, North Haven, CT (US); Kelly Barnes, Algonquin, IL (US); ElHadji Dioum, Chicago, IL (US); YiFang Chu, Glenview, IL (US)

(73) Assignee: Stokely-Van Camp, Inc., Chicago, IL (US)

( * ) Notice: Subject to any disclaimer, the term of this patent is extended or adjusted under 35 U.S.C. 154(b) by 1048 days.

(21) Appl. No.: 17/673,028

(22) Filed: Feb. 16, 2022

(65) Prior Publication Data

US 2023/0260600 A1     Aug. 17, 2023

(51) Int. Cl.
*G16C 20/30* (2019.01)
*G16B 5/00* (2019.01)
*G16H 20/60* (2018.01)

(52) U.S. Cl.
CPC ............... *G16C 20/30* (2019.02); *G16B 5/00* (2019.02); *G16H 20/60* (2018.01)

(58) Field of Classification Search
CPC .......... G16C 20/30; G16C 20/70; G16B 5/00; G16H 20/10; G16H 20/60
See application file for complete search history.

(56) References Cited

U.S. PATENT DOCUMENTS

| | | | |
|---|---|---|---|
| 8,340,944 B2 | 12/2012 | Jung et al. | |
| 10,769,246 B2 | 9/2020 | Viljoen et al. | |
| 2004/0001874 A1 | 1/2004 | Davidson et al. | |
| 2004/0067986 A1 | 4/2004 | Sassover | |
| 2005/0240355 A1 | 10/2005 | Brown et al. | |
| 2007/0214008 A1* | 9/2007 | Jung ....................... | A23L 33/30 600/300 |
| 2012/0265514 A1* | 10/2012 | Hopkins ................ | G16C 20/50 703/11 |
| 2013/0144887 A1 | 6/2013 | Chen et al. | |
| 2014/0114987 A1 | 4/2014 | Hoeng et al. | |

(Continued)

FOREIGN PATENT DOCUMENTS

WO      WO-2022147350 A1 *   7/2022   ............. A23L 33/15

OTHER PUBLICATIONS

Kharyuk et al., Employing fingerprinting of medicinal plants by means of LC-MS and machine learning for species identification task, Nov. 19, 2018, Nature.com, Scientific Reports (2018) 8:17053, pp. 1-12.*

(Continued)

*Primary Examiner* — Rehana Perveen
*Assistant Examiner* — John P Hocker
(74) *Attorney, Agent, or Firm* — Barnes & Thornburg LLP; Chloe Salome Margulis

(57) ABSTRACT

A system is configured to identify efficacious ingredients for functional blends by determining a rank of at least one functional ingredient using several pathway-based groups of functional ingredients. A rank of at least one functional ingredient is based on predicted activity of active compounds present in the at least one functional ingredient.

24 Claims, 6 Drawing Sheets

(56) References Cited

U.S. PATENT DOCUMENTS

| | | | |
|---|---|---|---|
| 2017/0169183 A1 * | 6/2017 | Koyama | G16C 20/60 |
| 2019/0025287 A1 * | 1/2019 | Laing | G01N 33/5044 |
| 2019/0355458 A1 | 11/2019 | Zhang et al. | |
| 2020/0227176 A1 | 7/2020 | Eifert et al. | |
| 2021/0057050 A1 * | 2/2021 | Zavoronkovs | C07D 409/12 |
| 2021/0287763 A1 | 9/2021 | Sharma | |
| 2025/0109105 A1 * | 4/2025 | Gokhale | C07D 403/04 |

OTHER PUBLICATIONS

Zhang et al. (Year: 2020), A Molecular-Level Food Adulteration Database in China Based on Molecular Fingerprints and Similarity Algorithms Prediction Expansion, Available Online: May 8, 2020, Food Chemistry, vol. 327, Oct. 15, 2020, 127010, pp. 1-7.*
Extended Search Report issued on Jul. 12, 2023 in EP Appl. No. 23153156.7.
Smith et al., "Functional Food Product Development," Prince Edward Island Food Technology Centre, Wiley-Blackwell, pp. 1-536, 2010.

* cited by examiner

700-A

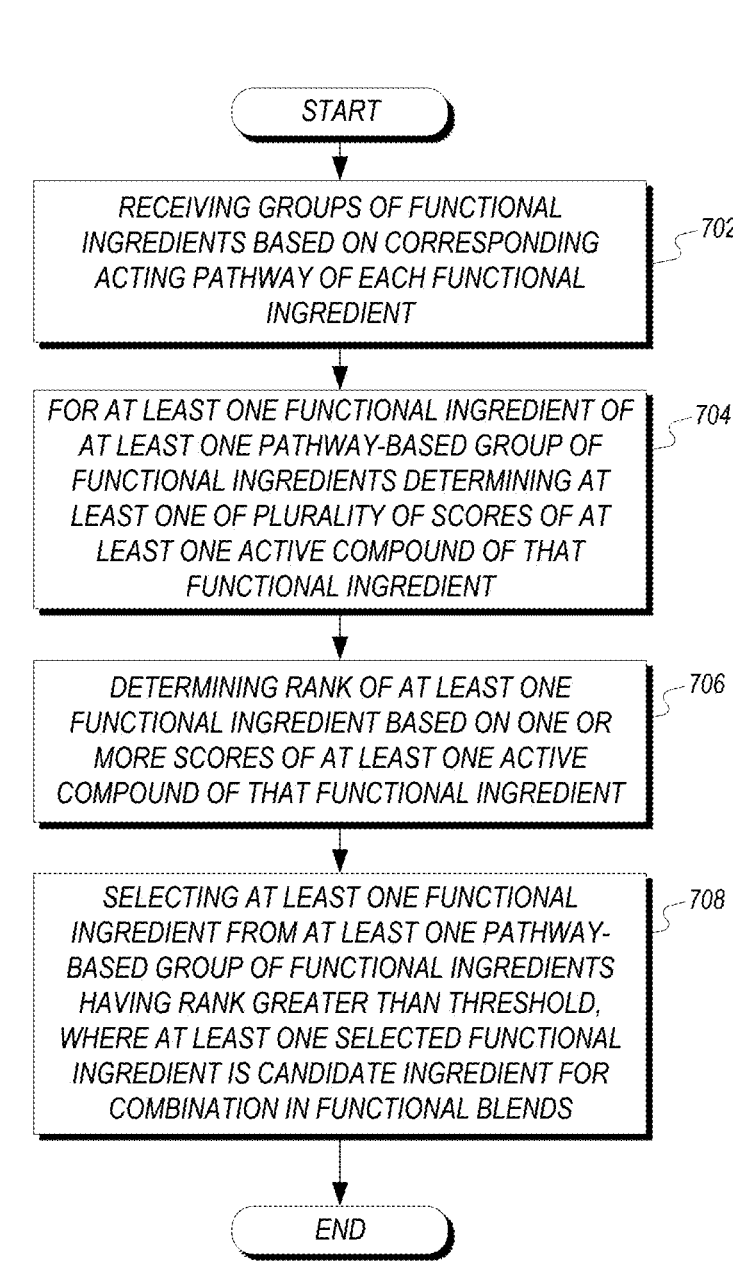

START

RECEIVING GROUPS OF FUNCTIONAL INGREDIENTS BASED ON CORRESPONDING ACTING PATHWAY OF EACH FUNCTIONAL INGREDIENT ⎯702

FOR AT LEAST ONE FUNCTIONAL INGREDIENT OF AT LEAST ONE PATHWAY-BASED GROUP OF FUNCTIONAL INGREDIENTS DETERMINING AT LEAST ONE OF PLURALITY OF SCORES OF AT LEAST ONE ACTIVE COMPOUND OF THAT FUNCTIONAL INGREDIENT ⎯704

DETERMINING RANK OF AT LEAST ONE FUNCTIONAL INGREDIENT BASED ON ONE OR MORE SCORES OF AT LEAST ONE ACTIVE COMPOUND OF THAT FUNCTIONAL INGREDIENT ⎯706

SELECTING AT LEAST ONE FUNCTIONAL INGREDIENT FROM AT LEAST ONE PATHWAY-BASED GROUP OF FUNCTIONAL INGREDIENTS HAVING RANK GREATER THAN THRESHOLD, WHERE AT LEAST ONE SELECTED FUNCTIONAL INGREDIENT IS CANDIDATE INGREDIENT FOR COMBINATION IN FUNCTIONAL BLENDS ⎯708

END

FIG. 7A

HIGH EFFICACY FUNCTIONAL INGREDIENT BLENDS

TECHNICAL FIELD

The present disclosure generally relates to identifying efficacious ingredients for high efficacy blends.

BACKGROUND

Consumers are searching for natural solutions to improve their well-being and health. Typically, blends of functional ingredients are marketed for a particular purpose based on the efficacy of the individual ingredients forming the blend rather than the efficacy of the blend "as a whole". It would be desirable to create blends of specific individual functional foods that, in combination, provide efficacious results.

SUMMARY

A system of the present disclosure is configured to identify efficacious ingredients for functional blends by determining a rank of functional ingredients using several pathway-based groups of functional ingredients. The ranking system may be based on predicted activity of active compounds present in that functional ingredient, and may further include a filter of blood-brain membrane barrier (BBB) permeability yielding a score which enables prediction of top candidates for functionality.

A system of the present disclosure is configured to identify efficacious ingredients for blends of functional ingredients. The system may include a database that includes data that indicates a plurality of functional ingredients where each functional ingredient has at least one active compound, and each functional ingredient affects a predefined organism function via a corresponding biological pathway. The system may also include an analytic device that is communicatively coupled to the database to receive data from the data base. The analytic device may be configured to (i) receive, from the database, a plurality of groups of functional ingredients, each group including a plurality of functional ingredients that affect the same organism function via the same corresponding biological pathway, (ii) for at least one active compound present in at least one functional ingredient of at least one pathway-based group of functional ingredients, determine at least a first score of the active compound, (iii) determine a first rank of the at least one functional ingredient of at least one pathway-based group based on the first score of the at least one active compound of the at least one functional ingredient, and/or (iv) generate a blend of two or more functional ingredients by selecting, from at least one pathway-based group, at least one functional ingredient having the first rank greater than a threshold.

A method of the present disclosure includes, receiving by a controller, a plurality of groups of functional ingredients with each group including a plurality of functional ingredients that affect a predefined organism function via the same corresponding biological pathway, and each functional ingredient having at least one active compound. The method may also include, determining a first score for one or more active compounds present in at least one functional ingredient of at least one of the plurality of pathway-based groups of functional ingredients. The method may also include determining a first rank of at least one functional ingredient based on the first score of the one or more active compounds present in the at least one functional ingredient, and generating a blend of two or more functional ingredients by selecting, from at least one pathway-based group of functional ingredients, at least one functional ingredient having the first rank greater than a threshold.

In other aspects, a system of the present disclosure may include a database that includes data indicating a plurality of functional ingredients with each functional ingredient having at least one active compound, and each functional ingredient affecting a predefined organism function via a corresponding biological pathway. The system may also include an analytic device that is configured to (i) receive, from the database, a plurality of groups of functional ingredients, each functional ingredient having at least one active compound, each functional ingredient affecting a predefined organism function via the same corresponding biological pathway, (ii) determine at least one score of one or more active compounds present in at least one functional ingredient of at least one of the plurality of pathway-based groups of functional ingredients, (iii) determine a rank of the at least one functional ingredient based on the at least one score of the one or more active compounds present in the at least one functional ingredient and (iv) generate a blend of two or more functional ingredients by selecting, from at least one of the plurality of pathway-based groups of functional ingredients, at least one functional ingredient having the rank greater than a threshold.

BRIEF DESCRIPTION OF THE DRAWINGS

The detailed description particularly refers to the following figures, in which:

FIG. 7A is a block diagram illustrating an exemplary process flow for generating functional ingredient blends;

DETAILED DESCRIPTION

Figure 1:
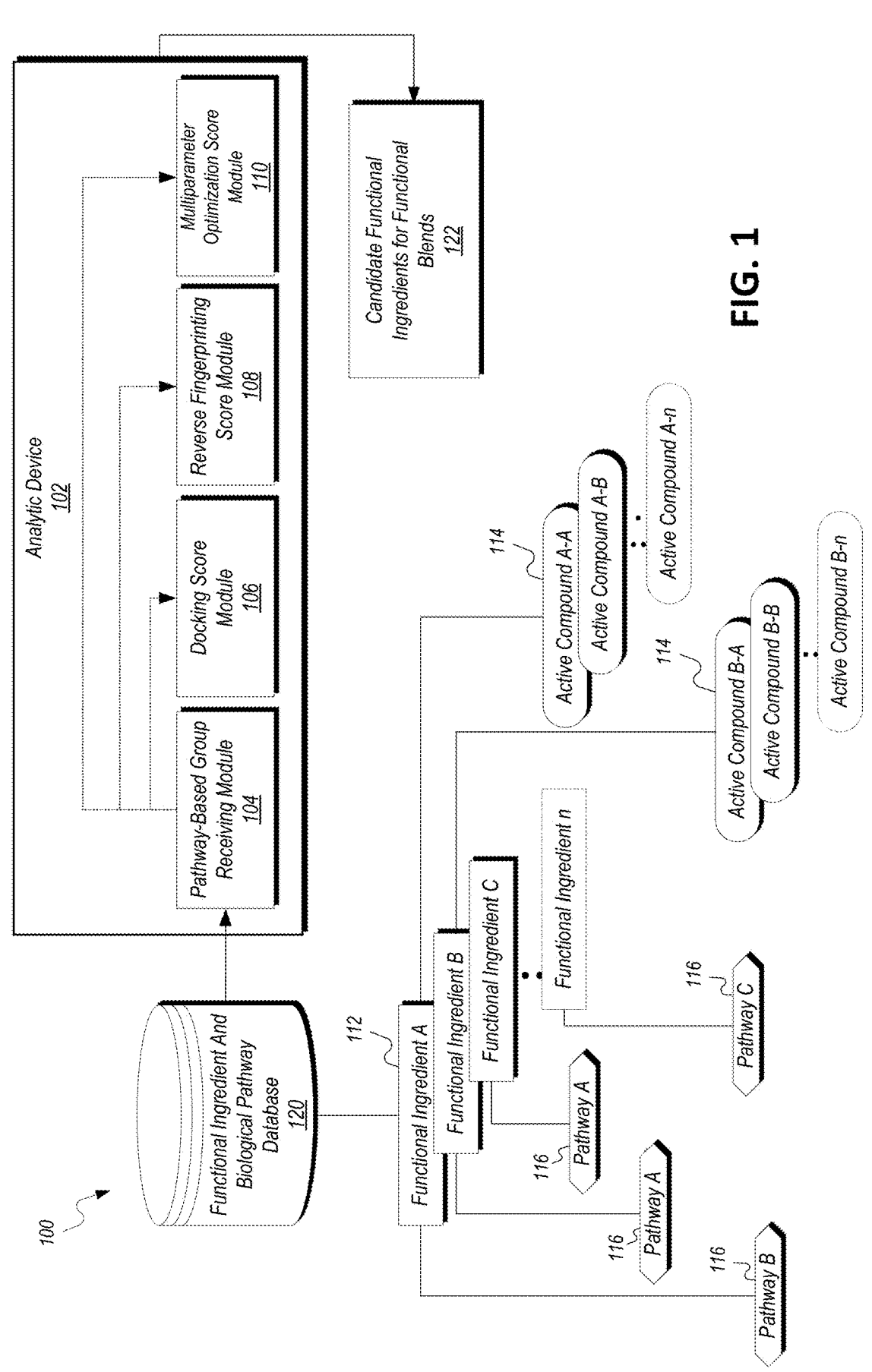
FIG. 1 is a block diagram illustrating an exemplary system for generating functional ingredient blends.

Natural ingredient combinations for inducing desirable body functions, such as increasing metabolism, providing relaxation, and so on, are in high demand. In some instances, functional ingredients capable of bringing about a desirable biological effect, such as relaxation and restful sleep, may number in the tens, hundreds, or more. Moreover, each functional ingredient may act through one or multiple mechanisms, both known and unknown, that may affect biological processes, such as metabolism or sleep, favorably or unfavorably.

Functional ingredients are a diverse group of compounds that are intended to produce a positive effect on the health of a consumer via physiological activity in the consumer body.

Functional ingredients include ingredients that influence health over and above a basic nutritional value of those ingredients. Put another way, functional ingredients may be bioactive ingredients or compounds obtainable from food sources and having a beneficial effect on health or mood beyond basic nutritional function. Examples of functional ingredients include vitamins.

Testing for the efficacy of functional ingredient combinations may require extensive experimentation, which is both expensive and time consuming. Traditional modeling of efficacy of functional ingredient combinations relies on existing data derived from in vitro and/or in vivo analysis. However, many ingredient combinations have not undergone such testing and, therefore, data regarding their combined performance is unavailable. As a result, touted effectiveness of many blends in the market is based on the efficacy of a single ingredient of the blend, rather than the efficacy of a combination of several ingredients. Accordingly, systems and methods for identifying efficacious ingredients for creating efficacious blends are needed.

Systems and methods of the present disclosure enable predicting efficacious ingredients as candidate ingredients for combination in efficacious ingredient blends. An efficacious ingredient blend includes a blend capable of having a significant biological effect that influences the health of a consumer of the blend in a manner over and above a basic nutritional value provided by each ingredient of that blend. As one example, the disclosed systems and methods use molecular modeling and machine learning to identify and rank expected activity of active compounds of functional ingredients. Accordingly, systems and methods of the present disclosure may enable identifying combinations of two or more functional ingredients for use in food and beverage products that may affect predefined organism or biological functions. Such predefined organism or biological functions, include but are not limited to sleep, relaxation, energy-boosting, focus, memory, metabolism, digestion, breathing, gut health, cognition, immunity, attentiveness, alertness, test performance, pain, anxiety, emotion, inflammation, drowsiness, insomnia, discomfort, stress, vitality, vigor, mental acuity, bone health, circulatory health, and vascular health.

As a result of such identification, certain combinations can be tested to demonstrate efficacy with respect to a predefined organism or biological function. In this regard, according to the described system and method a blend of functional ingredients are generated with a goal of producing a resulting blend of functional ingredients that contains individual functional ingredients whose individual impacts are at least substantially additive, if not synergistic. For example, assume ingredient W provides a +10 benefit for biological factor BF1, component X provides a +5 benefit for biological factor BF1 and a +15 benefit for biological factor BF2, component Y provides a +10 benefit for biological factor BF2, and component Z provides a +5 benefit for biological factor BF1 and a +20 benefit for biological factor BF3. A completely "additive" formulation of these three ingredients would provide a +20 benefit for biological factor BF1, a +25 benefit for biological factor BF2, and a +20 benefit for biological factor BF3 without requiring an increase in dosage of any of the four component functional ingredients.

Due to the interactions of functional ingredients and possible other drugs or pharmaceuticals in a body, it may be difficult to identify such beneficial additive or synergistic formulations of the blends of functional ingredients. Accordingly, the described system and method identify candidate functional ingredients to create, for example, additive (or synergistic) formulations of the blends of functional ingredients by identifying and selecting for the combination or blend, not only those functional ingredients that are effective and/or that are safe for use (alone and with each other), but also those functional ingredients that operate through substantially independent mechanisms of action in the body. In this manner, the individual functional ingredients are unlikely to interfere with one another in the body and thus produce a maximum positive result.

Turning now to FIG. 1, an exemplary system 100 for generating functional ingredient blends is illustrated. An analytic device 102 of the system 100 receives input from a functional ingredient and biological pathway database 120 and generates as an output of a plurality of candidate functional ingredients 122 for generating one or more blends of functional ingredients, i.e., functional ingredient blends. The skilled artisan will appreciate that the functional ingredient and biological pathway database 120 may be a single database or more than one database. The analytic device 102 may include a pathway-based group receiving module 104, a docking score module 106, a reverse fingerprinting score module 108, and a multi-parameter optimization score module 110. Of course, the system 100 may be implemented to include more or fewer components that are arranged differently with respect to one another and/or configured to perform combinations of functions consistent with the present disclosure. As described in reference to at least FIG. 2, one or more of the pathway-based group receiving module 104, the docking score module 106, the reverse fingerprinting score module 108, and the multi-parameter optimization score module 110 may be implemented, wholly or partly, within a compute device 202.

The functional ingredient and biological pathway database 120 of the system 100 includes a listing of a plurality of functional ingredients 112 that operate to activate, inhibit, increase, decrease, modulate, or otherwise affect a given biological process or function of an organism. Each functional ingredient 112 of the functional ingredient and biological pathway database 120 may affect a biological process or function of an organism using the same or different biological pathways 116 from those of another. The functional ingredient and biological pathway database 120 includes, for each functional ingredient 112, a listing of one or more active compounds 114 present in the functional ingredient 112. In one example, the functional ingredient and biological pathway database 120 may be implemented to be part of the data sources 206 described in reference to FIG. 2.

The pathway-based group receiving module 104 is communicatively coupled to the functional ingredient and biological pathway database 120 and is configured to request and receive data therefrom. In some instances, the pathway-based group receiving module 104 queries the functional ingredient and biological pathway database 120 for a plurality of groups of functional ingredients 112, where each group includes functional ingredients 112 that affect a given organism function using the same biological pathway. In some other instances, a first biological pathway used by functional ingredients of a first group of the plurality of groups may be different from a second biological pathway used by functional ingredients of a second group of the plurality of groups.

A biological pathway may be considered to be a molecular interaction that triggers, carries out, perpetuates, halts, or otherwise supports or inhibits a given biological process, including, but not limited to, activates, deactivates, turns on, turns off, modulates, and induces cellular movement or other activity. Examples of biological pathways include, but are not limited to, metabolic, gene-regulation, and signal transduction. The one or more functional ingredients 112 may have previously demonstrated a desired biological function through testing in functional, binding and other biological assays in vitro and/or in vivo. As just one example, a first biological pathway used by functional ingredients of a first pathway-based group may be the adenosine (Ado) pathway and a second biological pathway used by functional ingredients of a second pathway-based group may be the gamma-aminobutyric acid (GABA) pathway.

The pathway-based group receiving module 104 may also query the functional ingredient and biological pathway database 120 for one or more active compounds 114 present in each functional ingredient 112 of each pathway-based group of functional ingredients 112. An active compound 114 of an ingredient 112 may include a compound that effectively binds to, targets, modulates, or otherwise affects a given biological target.

The pathway-based group receiving module 104 is communicatively coupled to the docking score module 106, the reverse fingerprinting score module 108, and the multi-parameter optimization score module 110. The pathway-based group receiving module 104 may use at least one of the docking score module 106, the reverse fingerprinting score module 108, and the multi-parameter optimization score module 110 to evaluate one or more active compounds 114 and to associate a score with the one or more active compounds 114, based on the evaluation. In some instances, the score may be indicative of efficacy of the active compound 114 under predefined conditions.

Although the docking score module 106, the reverse fingerprinting score module 108, and the multi-parameter optimization score module 110, as illustrated in FIG. 1, are shown left-to-right and in order from the pathway-based group receiving module 104, the pathway-based group receiving module 104 may score one or more active compounds 114 using only one of the modules 106, 108, 110 or fewer than all the modules 106, 108, 110. Alternatively, the pathway-based group receiving module 104 may be configured to score one or more active compounds 114 using modules 106, 108, 110 in an order different from that illustrated in FIG. 1. As just one example, the pathway-based group receiving module 104 may score a given active compound (or a group of active compounds) 114 using, first, the reverse fingerprinting score module 108, then using the multi-parameter optimization score module 110, followed by using the docking score module 106.

The pathway-based grouping module 104 may use different score modules 106, 108, 110 to evaluate and score the one or more active compounds 114. In an example, the pathway-based group receiving module 104 may evaluate and score several of the one or more active compounds 114 using a first module of the score modules 106, 108, 110 and evaluate and score others of the one or more active compounds 114 using a second module of the score modules 106, 108, 110.

The analytic device 102 may associate a score (or a rank) with at least one functional ingredient 112 based on individual scores, or combinations of one or more scores, of the active compounds 114 present in the at least one functional ingredient 112. The analytic device 102 may then generate functional ingredient blends 122 by grouping a plurality of functional ingredients 112 having ranks greater than a predefined rank. In an example, the analytic device 102 may be configured to combine functional ingredients 112 from at least one of several different pathway-based groups into a single blend.

While not separately illustrated in FIG. 1, it is contemplated that the analytic device 102 may be configured to optimize blends of the generated candidate functional ingredients 122. In an example, optimizing combinations of the generated candidate functional ingredients 122 includes identifying potential interactions of two or more candidate functional ingredients with one another. As another example, optimizing the generated candidate functional ingredients 122 includes determining interactions that may occur between and among several pathways activated by the active compounds within the blend. As still another example, optimizing the generated candidate functional ingredients 122 includes determining the concentration of one or more active compounds in blends of two or more candidate functional ingredients. As yet another example, optimizing blends of the generated candidate functional ingredients 122 includes determining a concentration or dose of at least one functional ingredient in the blend. Other optimization strategies may include performing bioassay or clinical trial to identify possible side-effects and/or determining whether the generated functional ingredient blend is safe.

Figures 2, 3, 4:
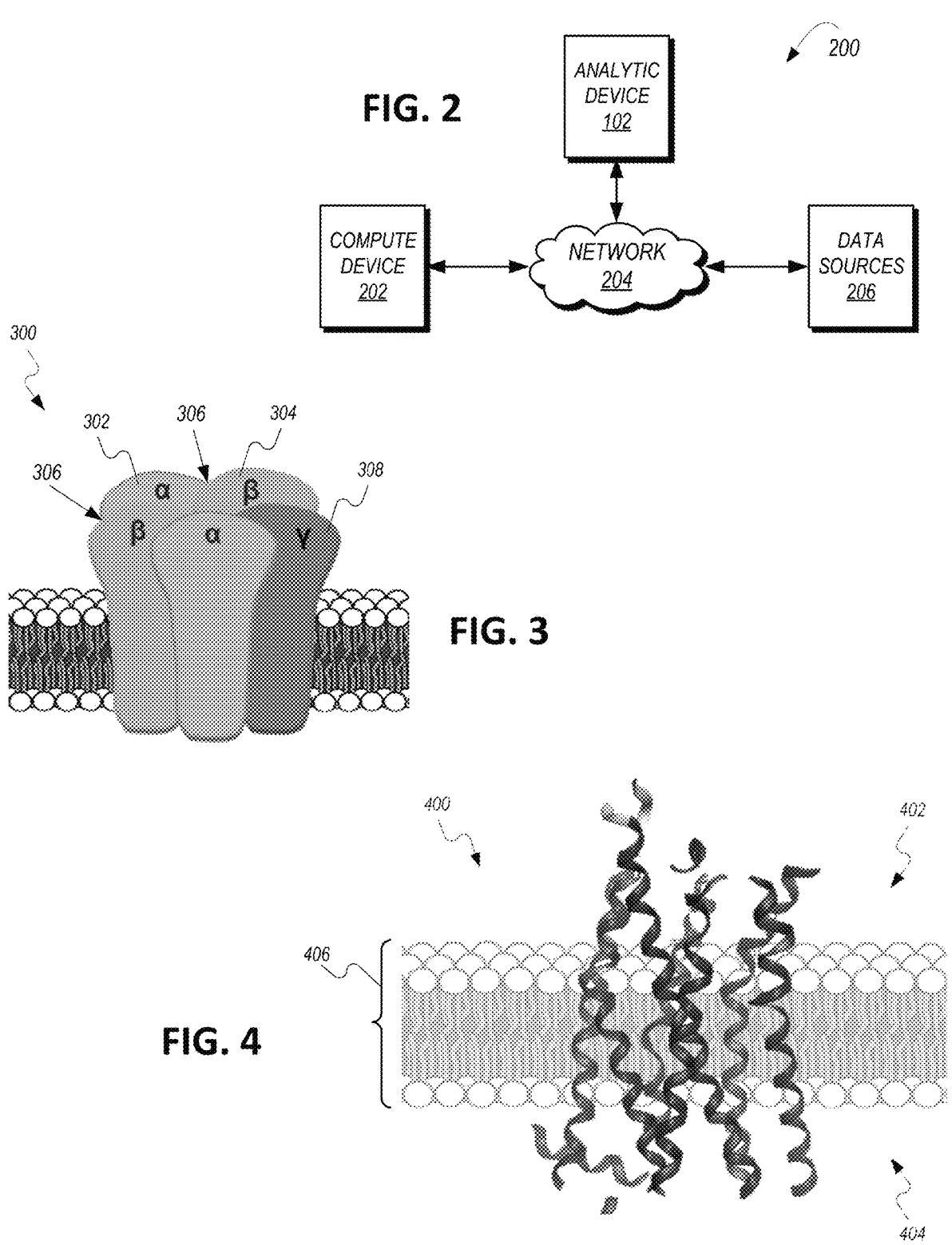
FIG. 2 is a block diagram illustrating a cooperative network of devices including the system of FIG. 1.
FIG. 3 is a block diagram illustrating an exemplary receptor of gamma-aminobutyric acid.
FIG. 4 is a block diagram illustrating an exemplary receptor of adenosine.

FIG. 2 illustrates an exemplary implementation 200 of a cooperative network of devices, including the analytic device 102, for generating functional ingredient blends. The system 200 includes a compute device 202 communicatively coupled, via a network 204, to the analytic device 102. The network 204 may be embodied as any type of network capable of communicatively connecting the compute device 202 and the analytic device 102, such as a cloud network, an Ethernet-based network, etc. Accordingly, the network 204 may be established through a series of links/interconnects, switches, routers, and other network devices which are capable of connecting the compute device 202 and the analytic device 102 of the network 204.

While FIG. 1 illustrates the pathway-based group receiving module 104, the docking score module 106, the reverse fingerprinting score module 108, and the multi-parameter optimization score module 110 being integral parts of the analytic device 102, the systems and methods of the present disclosure are not limited thereto. In other examples, the compute device 202 may include, or may be configured to perform operations of, one or more of the pathway-based group receiving module 104, the docking score module 106, the reverse fingerprinting score module 108, and the multi-parameter optimization score module 110, such that the compute device 202 and the analytic device 102 form a comprehensive data processing, analysis, and exchange system.

The compute device 202 and the analytic device 102 are communicatively coupled to at least one of a plurality of data sources 206. In one example, the functional ingredient and biological pathway database 120 of FIG. 1 may be implemented to include or to be part of the data sources 206. The data sources 206 comprise a variety of sources of data related to functional ingredients 112 and/or corresponding active compounds 114. At least one of the data sources 206 transmits data to the compute device 202. Once received, the compute device 202 may process the data (e.g., clean, harmonize, organize, prioritize, arrange in a hierarchy, categorize according to one or more attributes, etc.) prior to transmitting the data to the analytic device 102.

At least one of the data sources 206 transmits data directly to the analytic device 102. Once received, the analytic device 102 may perform analytics processes based on, or using, the received source data. The results of the analytics analysis output by the analytic device 102 may then be used for various purposes. For instance, the analytic device 102 may output the results of the analytics processes to the compute device 202 to effectuate identification of candidate functional ingredients for blend formation and production and optimization thereof. While not illustrated separately, the analytic device 102 may comprise (or be communicatively connected to) a data aggregation service, e.g., that executes on the network 204.

Each of the compute device 202 and the analytic device 102 may be embodied as any type of compute device capable of performing functions, including, but not limited to, a compute device, a storage device, a server (e.g., stand-alone, rack-mounted, blade, etc.), a sled (e.g., a compute sled, an accelerator sled, a storage sled, etc.), an enhanced network interface controller (NIC), a network appliance (e.g., physical or virtual), a router, a web appliance, a distributed computing system, a processor-based system, and/or a multiprocessor system.

Referring now to FIGS. 3 and 4, at least one rank of a given functional ingredient 112 indicates a docking score of one or more active compounds 114 of that functional ingredient 112. A docking score may be indicative of a level of interaction, e.g., potency, between the one or more active compounds 114 of a particular functional ingredient 112 and a target receptor within an organism such as a human body. As just one example, a mechanism of action (MoA) of the one or more active compounds of a functional ingredient with a target receptor may indicate a binding mode and binding affinity of a complex formed by two or more constituent molecules with known structures.

With reference to FIG. 3, functional ingredients impacting sleep may act through a GABA pathway, e.g., by acting on GABAA receptors. The GABAA receptor 300 is a molecular target for suppressing activity of a central nervous system. The GABAA receptors include five subunits—two alpha (α) subunits 302, two beta (β) subunits 304, and one gamma (γ) subunit 308 arranged around a central pore (not illustrated). The GABA neurotransmitter (ligand) binds at two sites (GABA sites) 306 disposed between a and B subunits 302, 304 causing the central pore, also referred to as a chloride channel (Cl⁻ channel) of the GABAA receptor, to open. Benzodiazepines-like neurotransmitters bind at a benzodiazepine (BDZ) site (not illustrated) located between the α and γ subunit. Other binding sites, such as for zinc, furosemide, volatile anesthetics and/or alcohols, and convulsants, are also present.

For a GABAA receptor 300, most of active compounds dock at binding sites 302, 304 different from that of the GABA molecule that docks at site 306. The active compounds may cooperate with the GABA molecule to increase a period of time during which the GABAA receptor channel is open. The GABA molecule changes the intracellular chlorine (Cl⁻) concentration to enhance the protein function for sleep.

As one example, a docking score may range between 0 and 10. In other examples, different ranges and/or values are also contemplated. In some instances, the docking scoring mechanism and ranking may be set up such that a docking score having a larger magnitude indicates a stronger interaction or a higher activity interaction, than a docking score having a smaller magnitude. The bioactivities of at least one functional ingredient 112 in GABA pathway-based group of functional ingredients 112 may be ranked based on bioactivities (as expressed, for example, by docking scores) of active compounds 114 of the at least one functional ingredient 112 in the GABA pathway.

One of skill will appreciate that within an organism such as the human body, there are many biological pathways and that the reference in FIG. 3 to the GABA pathway merely provides an example of how the docking score may be obtained for any particular pathway.

With reference to FIG. 4, functional ingredients affecting sleep may act through Ado pathway, e.g., by affecting Ado levels, by acting on Ado receptors. Adenosine receptor 400 is one of the G protein-coupled receptors (GPCRs), also known as seven-transmembrane domain receptors or G protein-linked receptors (GPLR). The GPCR receptors are receptors that extend to a surface 406 of a cell to detect molecules outside (extracellular to) 402 the cell and activate cellular (intracellular) 404 responses. Ligands can bind either to extracellular N-terminus and loops (e.g., glutamate receptors) or to the binding site within transmembrane helices.

In the Ado pathway, active compounds with this MoA may be docked to adenosine $A_{2A}$ and $A_1$ receptors, e.g., allosteric binding sites. Docking scores may be determined based on strength of binding between at least one active compound and the adenosine receptors. At least one functional ingredient 112 of adenosine pathway-based group of functional ingredients 112 may then be ranked based on the docking scores (such as, adenosine pathway docking scores) of the active compounds 114 present in the at least one functional ingredient 112.

Figure 5:
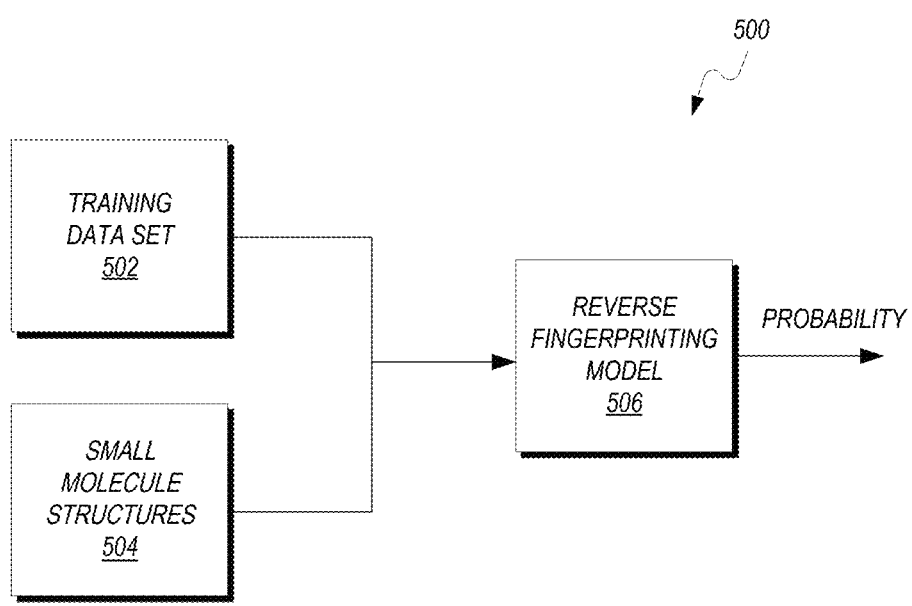
FIG. 5 is a block diagram illustrating an exemplary implementation of a reverse fingerprinting module.

FIG. 5 illustrates an exemplary implementation 500 for determining a reverse fingerprinting score by the reverse fingerprinting score module 108. Small molecules of active compounds can be represented using molecular descriptors, or molecular fingerprints, indicating physicochemical or structural features of molecules. Molecular fingerprints may be represented by bit strings, where each bit detects presence or absence of a specific chemical feature or represents a value range of a property descriptor.

Determining a reverse fingerprinting score includes evaluating bit patterns in active compounds being scored. The reverse fingerprinting score module 108 is configured to determine a reverse fingerprinting score by comparing a frequency of each bit position within the scored active compound and a frequency of the position within bit strings of reference molecules. For example, assigned bits may be indicative of features of the molecule such as functional groups, pharmacophore triangles and concentric circles. A reverse fingerprint score indicates a probability (likelihood) of a given active compound to perform specific function.

In one example, the reverse fingerprinting score module 108 includes a training data database 502, small molecule structures 504, and a reverse fingerprinting model 506. The training data database 502 includes digital molecular fingerprint data generated based on the molecular structure of several compounds. The reverse fingerprinting model 506 may be trained using the training data set 502. In addition to the training data, the reverse fingerprinting model 506 is configured to receive, as input, the small molecule structures 504 of the one or more active compounds 114. The reverse fingerprinting model 506 is configured to output a probability value, which may be used to rank the ingredients.

The reverse fingerprinting module 108 scores the activity of at least one active compound for virtual screening, narrowing down and ranking the functional ingredients to be chosen for a blend combination, and predicting the activity of new functional ingredients. The docking score and the reverse fingerprinting score indicate an expected activity of a particular active compound. Moreover, both scores may be based on the performance or efficacy of a particular active compound within an identified pathway. Under the method of the present disclosure the same active compound may have a different score for at least one of differing pathways.

With reference to FIGS. 6A-6F, the multi-parameter optimization score module 110 determines a membrane barrier score of one or more of the active compounds 114. A membrane barrier score of the one or more active compounds 114 of a given functional ingredient 112 indicates the capability of that active compound to cross the blood-brain membrane barrier. A multi-parameter optimization score is indicative of the ability of the active compound to cross the blood-brain membrane barrier to reach the central nervous system. FIGS. 6A-6F illustrate exemplary piecewise linear transformational functions with values between 0 and 1. Each transformational function indicates a range of values spanned by a given physicochemical property of a compound, including the most and least desirable values from an optimization standpoint.

Figure 6C:
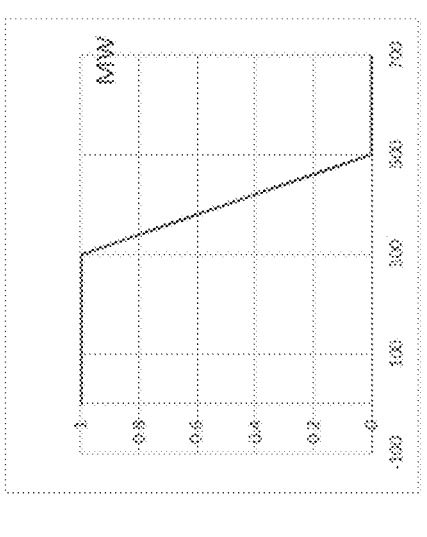
FIGS. 6A-6F are graphs illustrating exemplary ranges of parameters for determining a multi-parameter optimization score.
Figure 6F:
Figure 6B:
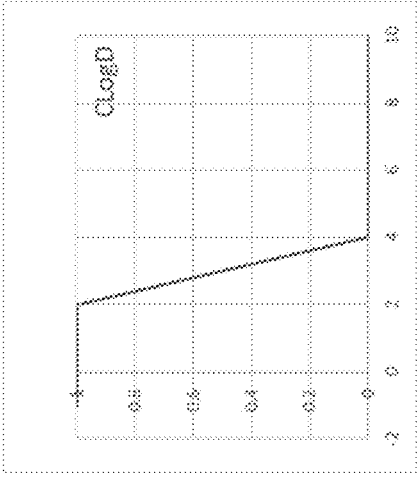
Figure 6E:
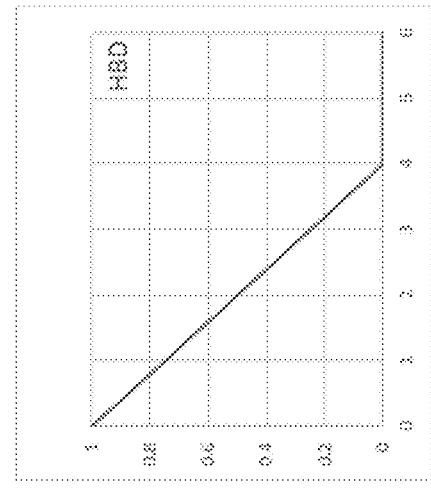
Figure 6A:
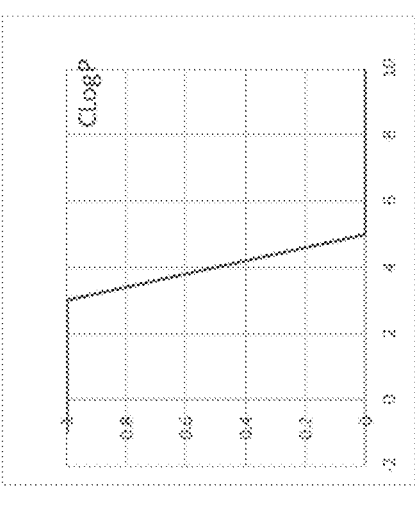
Figure 6D:
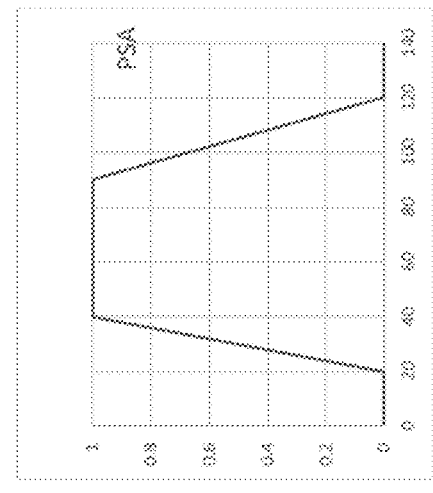

FIG. 6A illustrates a range of values of lipophilicity (C log P). FIG. 6B illustrates a calculated distribution coefficient at pH 7.4 (C log D). FIG. 6C illustrates the molecular weight (MW) of the active compound. FIG. 6D illustrates the topological polar surface area (PSA) of the active compound. FIG. 6E illustrates a range of a number of hydrogen-bond donors (HBD). FIG. 6F illustrates the acid-base dissociation constant (pKa) value range of a most basic center molecule of the compound.

The multi-parameter optimization score module 110 may eliminate a functional ingredient 112 from among the potential candidate functional ingredients if one or more of its active compounds present in the corresponding potential candidate functional ingredient has a blood-brain membrane barrier score greater than or less than a predefined value. A blood-brain membrane barrier score may be determined by molecular structure properties of the one or more active compounds. The blood-brain membrane barrier score may be independent of the activity of the one or more active compounds within any particular biological pathway.

For example, ranking and selecting based on at least one mechanism of action and pathway may be indicative of top (i.e., more preferred) functional ingredient candidates. The identified functional ingredient candidates may then be evaluated based on one or more other factors, such as, but not limited to, dosage, safety, and stability. The systems and methods of the present disclosure enable identifying high efficacy functional ingredient blends using categorization and ranking of active compounds of individual functional ingredients.

FIG. 7A illustrates an exemplary process 700-A for generating functional ingredient blends in accordance with the present disclosure. In some embodiments, the process 700-A may be executed by one or more processors of the analytic device 102 using data sources and/or one or more modules of the analytic device 102 (e.g., the functional ingredient and biological pathway database 120, the pathway-based group receiving module 104, the docking score module 106, the reverse fingerprinting score module 108, and the multi-parameter optimization score module 110). The process 700-A may begin at block 702 where the analytic device 102 receives, e.g., from the input data from the data sources 206 such as the functional ingredients and biological pathway database 120, a plurality groups of functional ingredients 112 as potential candidates for a combination in a functional ingredient blend. In some instances, at least one group combines the plurality of functional ingredients 112 that use the same biological pathway to achieve one or more desired effects of the functional ingredient 112 on an organism, such as to activate, inhibit, increase, decrease, modulate, or otherwise affect a given biological process or function of an organism.

At block 704, the analytic device 102 determines at least one of a plurality of scores for one or more of the active compounds 114 of at least one of the plurality of functional ingredients 112 of at least one pathway-based group of functional ingredients 112. As described in reference to at least FIG. 7B, the analytic device 102 may determine, for the at least one active compound 114, at least one of a docking score, a reverse fingerprinting score, and a multi-parameter optimization score. At block 706, the analytic device 102 ranks the at least one functional ingredient 112 based on the at least one of the plurality of scores of the at least one active compound 114 of the at least one functional ingredient 112. The analytic device 102, at block 708, selects, from at least one pathway-based group, one or more functional ingredients 112 having a rank greater than a threshold, where the selected functional ingredients are candidate ingredients for combination in functional ingredient blends.

The process 700-A may then end. In other examples, the process 700-A may be repeated in response to a receipt, by the analytic device 102, of a plurality of pathway-based groups, each group including one functional ingredient 112 or more than one functional ingredient 112, i.e., a plurality of functional ingredients 112, or in response to a receipt of different data or signal.

Figure 7B:
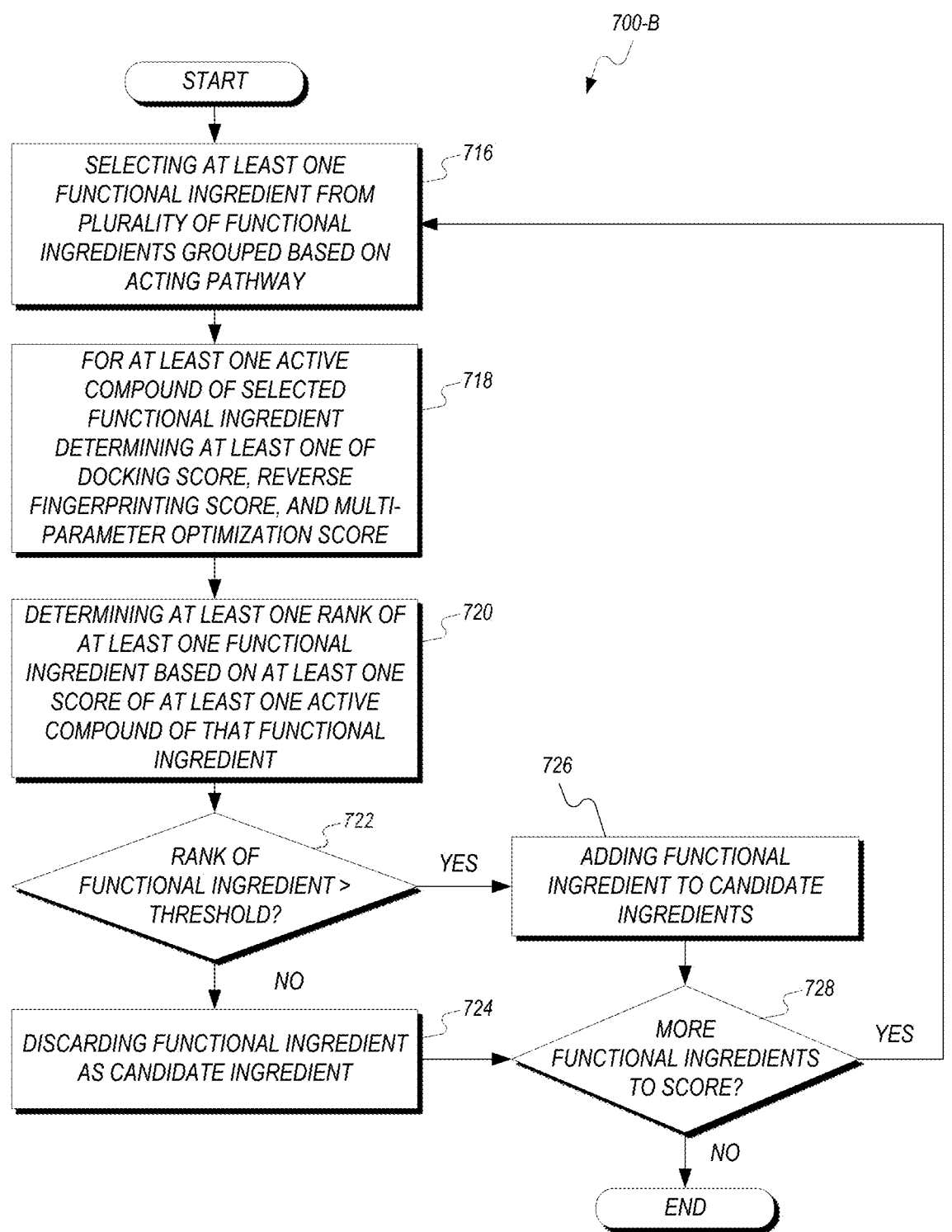
FIG. 7B is a block diagram illustrating an exemplary process flow for generating determining scores of active compounds for generating functional ingredient blends.

FIG. 7B illustrates an exemplary process 700-B for determining scores of active compounds 114 for identifying candidate functional ingredient for combination in functional ingredient blends. One or more operations of the process 700-B may be performed by the analytic device 102 at block 704 described in reference to FIG. 7A. The process 700-B begins at block 716 where the analytic device 102 selects a first functional ingredient of a plurality of functional ingredients 112 within a given pathway-based group in accordance with the present disclosure.

The analytic device 102, at block 718, determines at least one of a docking score, a reverse fingerprinting score, and a multi-parameter optimization score of at least one of the plurality of active compounds 114. In one example, a docking score of a given active compound 114 indicates a level of interaction, e.g., potency, between that active compound 114 and a target receptor of an organism such as a human body.

In another example, to determine a reverse fingerprinting score of the one or more active compounds 114 of the selected functional ingredient 112, the analytic device 102 compares a bit string of the active compound being scored (scored active compound) to bit strings of reference molecules. In particular, the analytic device 102 may compare a frequency of each bit position within the scored active compound to the frequency of the position in bit strings of the reference molecules.

In still another example, the analytic device 102 determines the multi-parameter optimization score of a given active compound 114 by evaluating how quickly and/or how completely that active compound crosses a blood-brain membrane barrier. At block 720, the analytic device 102 determines ranks of the selected functional ingredient 112 based on at least one score of the one or more of the active compounds 114 of that functional ingredient 112.

The analytic device 102, at block 722, determines whether the rank of the selected functional ingredient is greater than a predefined threshold. In response to the rank of the selected functional ingredient 112 being less than a threshold, the analytic device 102, at block 724, discards the selected functional ingredient 112 as a candidate ingredient 122 for combination in a functional ingredient blend.

In response to the selected functional ingredient 112 being greater than a threshold, the analytic device 102, at block 726, adds the selected functional ingredient 112 as a candidate ingredient 122 for generating a functional ingredient blend. The process 700-B may then proceed to block 728 where the analytic device 102 determines whether more functional ingredients 112 are desired to be scored. If another functional ingredient is desired to be scored, the process 700-B returns to block 716 where the analytic device 102 selects a next functional ingredient 112. If no other functional ingredients remain to be scored within a given pathway-based group, the analytic device 102 may exit the process 700-B.

The process 700-B may then end. In other examples, the process 700-B may be repeated in response to a determination, by the analytic device 102, that a plurality of functional ingredients 112 in several pathway-based groups may be tested as candidates for combination in a functional ingredient blend. The process 700-B may also be repeated in response to a different determination or signal.

Figure 8:
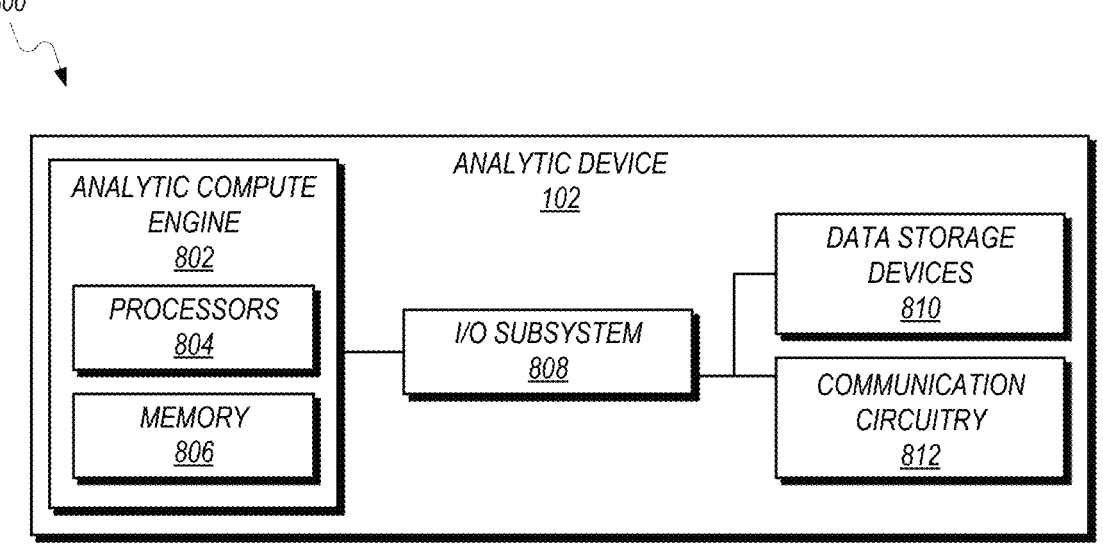
FIG. 8 is a block diagram illustrating an exemplary implementation of an analytic device of the system of FIG. 1.

FIG. 8 illustrates an exemplary implementation 800 of the analytic device 102. While the illustrated implementation 800 describes only the analytic device 102, in other examples, the compute device 202 may be embodied to include similar components configured to perform similar operations to those described with respect to the analytic device 102. The analytic device 102 includes an analytic compute engine 802, an I/O subsystem 808, one or more data storage devices 810, and communication circuitry 812. It will be appreciated that the analytic device 102 may include other or additional components, such as those commonly found in a typical computing device (e.g., various input/output devices and/or other components), in other embodiments. Additionally, in some embodiments, one or more of the illustrative components may be incorporated in, or otherwise form a portion of, another component.

The analytic compute engine 802 may be embodied as any type of device or collection of devices capable of performing the described various compute functions, such as, but not limited to, compute functions related to or bearing on one or more of receiving a plurality of groups of functional ingredients, functional ingredients of a given group of functional ingredients affecting a same predefined organism function and each functional ingredient including a plurality of active compounds associated with that functional ingredient, determining one or more scores of at least one active compound of at least one functional ingredient of at least one pathway-based group of functional ingredients, determining one or more ranks of at least one functional ingredient based on the one or more scores of at least one active compound of the at least one functional ingredient, and generating a blend of two or more functional ingredients from at least one functional ingredient of at least one pathway-based group of functional ingredients having one or more ranks greater than a threshold.

In some embodiments, the analytic compute engine 802 may be embodied as a single device, such as an integrated circuit, an embedded system, a field-programmable gate array (FPGA), a system-on-a-chip (SOC), an application-specific integrated circuit (ASIC), reconfigurable hardware or hardware circuitry, or other specialized hardware to facilitate performance of the functions described herein. In some embodiments, the analytic compute engine 802 may include, or may be embodied as, one or more processors 804 (i.e., one or more central processing units (CPUs)) and memory 806.

The processor(s) 804 may be embodied as any type of processor capable of performing the described functions, such as, but not limited to, functions related to or bearing on receiving, processing, or otherwise manipulating, and/or transmitting data to facilitate one or more of receiving at least one group of functional ingredients, where a group may include one functional ingredient or more than one functional ingredient, where each functional ingredient may include one or more active compounds associated with that functional ingredient, and where each functional ingredient of a given group of functional ingredients affects a predefined organism function using one and/or same biological pathway, determining one or more scores of at least one active compound of at least one functional ingredient of at least one pathway-based group of functional ingredients, determining one or more ranks of at least one functional ingredient based on the one or more scores of at least one active compound of that functional ingredient, and generating a blend of two or more functional ingredients from functional ingredients having one or more ranks greater than a threshold. For example, the processor(s) 804 may be embodied as one or more single-core processors, one or more multi-core processors, a digital signal processor, a microcontroller, or other processor or processing/controlling circuit(s). In some embodiments, the processor(s) 804 may be embodied as, include, or otherwise be coupled to an FPGA, an ASIC, reconfigurable hardware or hardware circuitry, or other specialized hardware to facilitate performance of the described functions.

The memory 806 may be embodied as any type of volatile (e.g., dynamic random access memory (DRAM), etc.) or non-volatile memory or data storage capable of performing the described functions, such as, but not limited to, functions related to or bearing on storing, writing, erasing, overwriting, aggregating, buffering, or otherwise manipulating data to facilitate one or more of receiving a plurality of groups of functional ingredients, where each group includes one or more functional ingredients and each functional ingredient includes one or more active compounds associated with that functional ingredient, and where one or more functional ingredients of a given group affects a predefined organism function using a same corresponding biological pathway, determining one or more scores of at least one active compound of at least one functional ingredient of at least one pathway-based group of functional ingredients, determining one or more ranks of at least one functional ingredient based on the one or more scores of at least one active compound of that functional ingredient, and generating a blend of two or more functional ingredients by combining at least one functional ingredient having one or more ranks greater than a threshold. It will be appreciated that the memory 806 may include main memory (i.e., a primary memory) and/or cache memory (i.e., memory that can be accessed more quickly than the main memory). Volatile memory may be a storage medium that requires power to maintain the state of data stored by the medium. Non-limiting examples of volatile memory may include various types of random access memory (RAM), such as DRAM or static random access memory (SRAM).

The analytic compute engine 802 is communicatively coupled to other components of the analytic device 102 via the I/O subsystem 802, which may be embodied as circuitry and/or components to facilitate input/output operations with the processor 804, the memory 806, and other components of the analytic device 102. For example, the I/O subsystem 808 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some embodiments, the I/O subsystem 808 may form a portion of a system-on-a-chip (SoC) and be incorporated, along with the analytic compute engine 802 (e.g., the processor 804, the memory 806, etc.) and/or other components of the analytic device 102, on a single integrated circuit chip.

The one or more data storage devices 810 may be embodied as any type of storage device(s) configured for short-term or long-term storage of data, such as, for example, memory devices and circuits, memory cards, hard disk drives, solid-state drives, or other data storage devices. Each data storage device 810 may include a system partition that stores data and firmware code for the data storage device 810. Each data storage device 810 may also include an operating system partition that stores data files and executables for an operating system.

The communication circuitry 812 may be embodied as any communication circuit, device, or collection thereof, capable of enabling communications between the analytic device 102 and other computing devices, such as the compute device 202, the data sources 206, etc., as well as any network communication enabling devices, such as a gateway, an access point, other network switches/routers, etc., to allow ingress/egress of network traffic. Accordingly, the communication circuitry 812 may be configured to use any one or more communication technologies (e.g., wireless or wired communication technologies) and associated protocols (e.g., Ethernet, Bluetooth®, Wi-Fi®, WiMAX, LTE, 5G, etc.) to effect such communication.

It should be appreciated that, in some embodiments, the communication circuitry 812 may include specialized circuitry, hardware, or combination thereof to perform pipeline logic (e.g., hardware algorithms) for performing the functions described herein, including processing network packets (e.g., parse received network packets, determine destination computing devices for each received network packets, forward the network packets to a particular buffer queue of a respective host buffer of the analytic device 102, etc.), performing computational functions, etc.

In some embodiments, performance of one or more of the functions of the described communication circuitry 812 may be performed by specialized circuitry, hardware, or combination thereof of the communication circuitry 812, which may be embodied as a system-on-a-chip (SoC) or otherwise form a portion of a SoC of the analytic device 102 (e.g., incorporated on a single integrated circuit chip along with a processor 804, the memory 806, and/or other components of the analytic device 102). Alternatively, the specialized circuitry, hardware, or combination thereof may be embodied as one or more discrete processing units of the analytic device 102, each of which may be capable of performing one or more of the described functions.

A process for optimizing generated blends includes grouping one or more functional ingredients based on biological pathways by which these functional ingredients affect a predefined organism function. The most potent functional ingredient, e.g., functional ingredient having a highest rank and/or functional ingredient including active compound having a highest score, from at least one pathway-based group of functional ingredients may then be selected. This approach allows for substitution of one functional ingredients with another functional ingredient from the same pathway-based group of functional ingredients, such as when a given functional ingredient is prohibitively expensive, inaccessible, or for any other reason.

Another example of optimization includes using ingredients that affect a given organism function using multiple pathways, such as, but not limited to, Vitamin B6. In this approach, the selected multi-pathway ingredient may increase efficacy of the blend without increasing the number of ingredients within the blend.

Still another optimization strategy includes modifying an amount of an ingredient within a blend based on amounts of active compounds within the ingredient. In other words, optimization may include using desired amounts of active compounds as controls for determining an amount of ingredient within the blend.

Yet another exemplary improvement and optimization strategy includes conducting a design of an experiment (DOE) to identify ways to improve efficacy of a given blend or to alter ingredients of the blend while maintaining a predefined efficacy level.

While the concepts of the present disclosure are susceptible to various modifications and alternative forms, specific exemplary embodiments are been shown by way of example in the drawings and will be described. It should be understood, however, that there is no intent to limit the concepts of the present disclosure to the particular forms disclosed; on the contrary, the intention is to cover all modifications, equivalents, and alternatives falling within the spirit and scope of the invention as defined by the appended claims.

References in the specification to "one embodiment," "an embodiment," "an illustrative embodiment," etc., indicate that the described embodiment may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C): (A and B); (B and C); (A and C); or (A, B, and C). Similarly, items listed in the form of "at least one of A, B, or C" can mean (A); (B); (C): (A and B); (B and C); (A and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A system comprising:
a database including data indicating a plurality of functional ingredients, each functional ingredient having at least one active compound, and each functional ingredient affecting a predefined organism function via a corresponding biological pathway; and
an analytic device communicatively coupled to the database to receive data therefrom, wherein the analytic device comprises processors and memory storing instructions that, when executed by the processors, causes the analytic device to:
receive, from the database, a plurality of groups of functional ingredients, each group including a plurality of functional ingredients that affect a same organism function via a same corresponding biological pathway,
for each active compound present in each of the functional ingredients, determine a reverse fingerprinting score of the active compound, wherein determining the reverse fingerprinting score of the active compound comprises:
representing, by the analytic device and without human input, molecular descriptors of physicochemical or structural features of molecules of the active compound as a plurality of bit strings;
identifying, by the analytic device and without human input, whether each bit in the plurality of bit strings corresponds to presence or absence of a particular physicochemical or structural feature for producing a food product; and
evaluating, by the analytic device and without human input, a frequency of bit positions corresponding to the particular physicochemical or structural feature in the plurality of bit strings to generate the reverse fingerprinting score of the active compound,
determine a rank of each of the functional ingredients based on the respective reverse fingerprinting score,
generate a blend of functional ingredients based on selecting at least one functional ingredient amongst the plurality of functional ingredients having a rank greater than a threshold rank, and return the blend of functional ingredients for use in creating the food product with the at least one functional ingredient in the blend of functional ingredients.

2. The system of claim 1, wherein the predefined organism function is selected from sleep, metabolism, gut health, cognition, immunity, attentiveness, alertness, test performance, relaxation, pain, anxiety, inflammation, drowsiness, insomnia, discomfort, stress, vitality, vigor, mental acuity, bone health, circulatory health, and vascular health.

3. The system of claim 1, wherein the analytic device is further configured to determine, for each active compound present in each of the functional ingredients, at least one of (i) a docking score indicating a level of interaction of the active compound with a target receptor or (ii) a multi-parameter optimization score indicating ability of the active compound to cross a blood-brain membrane barrier.

4. The system of claim 3, wherein the analytic device is configured to, for each active compound present in each of the functional ingredients, determine a second score that differs from the reverse fingerprinting score, determine a second rank of each of the functional ingredients based on the reverse fingerprinting score and the second score, and generate the blend of functional ingredients by selecting, from at least one pathway-based group, at least one functional ingredient having the rank greater than the threshold rank.

5. The system of claim 4, wherein the second score is one of (i) a docking score indicating a level of interaction of the active compound with a target receptor, (ii) a second reverse fingerprinting score indicating a difference between a molecular fingerprint of the active compound and a reference fingerprint of a reference compound, or (iii) a multi-parameter optimization score indicating ability of the active compound to cross a blood-brain membrane barrier and differs from the reverse fingerprinting score.

6. The system of claim 5, wherein the analytic device is further configured to determine a third score that differs from the reverse fingerprinting score and the second score, determine a third rank of each of the functional ingredients based on the reverse fingerprinting score, the second score, and the third score, and generate the blend of functional ingredients by selecting, from at least one pathway-based group, at least one functional ingredient having the rank greater than the threshold rank.

7. The system of claim 6, wherein the third score is one of (i) a docking score indicating a level of interaction of the active compound with a target receptor, (ii) another reverse fingerprinting score indicating a difference between a molecular fingerprint of the active compound and a reference fingerprint of a reference compound, or (iii) a multi-parameter optimization score indicating ability of the active compound to cross a blood-brain membrane barrier and differs from the reverse fingerprinting score and the second score.

8. The system of claim 1, wherein the predefined organism function is selected from one of sleep and metabolism.

9. The system of claim 8, wherein one of the biological pathways is an adenosine (Ado) pathway.

10. The system of claim 9, wherein one of the biological pathways is a gamma-aminobutyric acid (GABA) pathway.

11. A method comprising:
receiving, by a controller, a plurality of groups of functional ingredients, each group including a plurality of functional ingredients that affect a predefined organism function via a same corresponding biological pathway, and each functional ingredient having at least one active compound, for each active compound in each of the functional ingredients, determining a reverse fingerprinting score of the active compound, wherein determining the reverse fingerprinting score of the active compound comprises:

representing, by the controller and without human input, molecular descriptors of physicochemical or structural features of molecules of the active compound as a plurality of bit strings;

identifying, by the controller and without human input, whether each bit in the plurality of bit strings corresponds to presence or absence of a particular physicochemical or structural feature for producing a food product; and evaluating, by the controller and without human input, a frequency of bit positions corresponding to the particular physicochemical or structural feature in the plurality of bit strings to generate the reverse fingerprinting score of the active compound, determining a rank of each of the functional ingredients based on the respective reverse fingerprinting score, generating a blend of functional ingredients based on selecting at least one functional ingredient among the plurality of functional ingredients having a rank greater than a threshold rank, and returning the blend of functional ingredients for use in creating the food product with the at least one functional ingredient in the blend of functional ingredients.

12. The method of claim 11, wherein the predefined organism function is selected from sleep, metabolism, gut health, cognition, immunity, attentiveness, alertness, test performance, relaxation, pain, anxiety, inflammation, drowsiness, insomnia, discomfort, stress, vitality, vigor, mental acuity, bone health, circulatory health, and vascular health.

13. The method of claim 11, further comprising determining, for each active compound present in each of the functional ingredients, at least one of (i) a docking score indicating a level of interaction of the at least one active compound with a target receptor or (ii) a multi-parameter optimization score indicating ability of the at least one active compound to cross a blood-brain membrane barrier.

14. The method of claim 13 further comprising, for each active compound present in each of the functional ingredients, determine a second score that differs from the reverse fingerprinting score, determine a second rank of each of the functional ingredients based on the reverse fingerprinting score and the second score, and generate the blend of functional ingredients by selecting, from at least one pathway-based group, at least one functional ingredient having the rank greater than the threshold rank.

15. The method of claim 14, wherein the second score is one of (i) a docking score indicating a level of interaction of the active compound with a target receptor, (ii) a second reverse fingerprinting score indicating a difference between a molecular fingerprint of the active compound and a reference fingerprint of a reference compound, or (iii) a multi-parameter optimization score indicating ability of the active compound to cross a blood-brain membrane barrier and differs from the reverse fingerprinting score.

16. The method of claim 15 further comprising determining a third score that differs from the reverse fingerprinting score and the second score, determine a third rank of each of the functional ingredients based on the reverse fingerprinting score, the second score, and the third score, and generate the blend of functional ingredients by selecting, from at least one pathway-based group, at least one functional ingredient having the rank greater than the threshold rank.

17. The method of claim 16, wherein the third score is one of (i) a docking score indicating a level of interaction of the active compound with a target receptor, (ii) another reverse fingerprinting score indicating a difference between a molecular fingerprint of the active compound and a reference fingerprint of a reference compound, or (iii) a multi-parameter optimization score indicating ability of the active compound to cross a blood-brain membrane barrier and differs from the reverse fingerprinting score and the second score.

18. The method of claim 11, wherein the predefined organism function is selected from one of sleep and metabolism.

19. The method of claim 18, wherein one of the biological pathways is an adenosine (Ado) pathway.

20. The method of claim 19, wherein one of the biological pathways is a gamma-aminobutyric acid (GABA) pathway.

21. The system of claim 1, wherein determining the reverse fingerprinting score of the active compound further comprises determining (i) a level of interaction between the active compound and a target receptor or (ii) a difference between a molecular fingerprint of the active compound and a reference fingerprint of a reference compound.

22. The system of claim 1, wherein determining the reverse fingerprinting score of the active compound further comprises determining an ability of the active compound to cross a blood-brain membrane barrier.

23. The system of claim 1, wherein the evaluating comprises providing the plurality of bit strings to a model that is trained to output an indication of whether each bit in the plurality of bit strings corresponds to the presence or the absence of the particular physicochemical or structural feature for producing the food product.

24. The system of claim 1, wherein the reverse fingerprinting score is determined based on a comparison of (i) a frequency of each bit position in the plurality of bit strings and (ii) a frequency of each bit position within bit strings of reference molecules, wherein the reverse fingerprinting score is a probability value.

* * * * *